Figure 1:
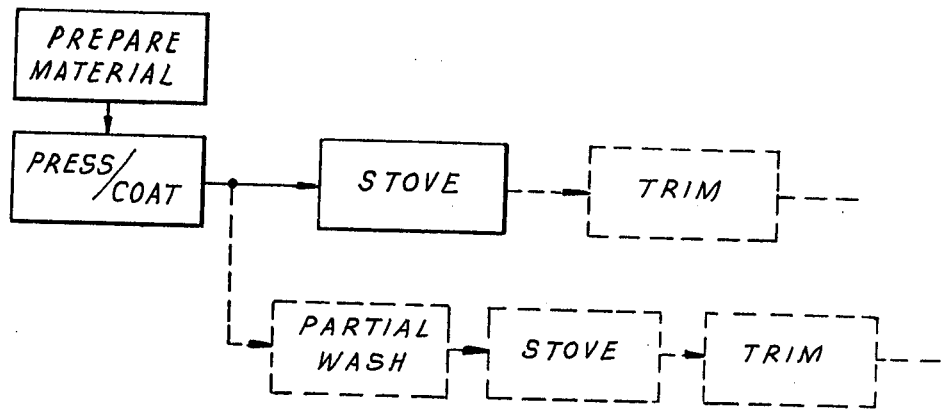

United States Patent [19]

Fidler et al.

[11] 4,108,099
[45] Aug. 22, 1978

[54] METHOD AND APPARATUS FOR FORMING A COATED CONTAINER

[75] Inventors: Fred Fidler, Cuffley; Joseph C. Holt, Greenford, both of England

[73] Assignee: Metal Box Limited, England

[21] Appl. No.: 733,275

[22] Filed: Oct. 18, 1976

[51] Int. Cl.² .......................................... B21D 51/26
[52] U.S. Cl. ........................ 113/120 A; 113/120 H; 427/358
[58] Field of Search ............... 113/120 A, 120 H; 72/41, 46, 42; 252/49.3, 49.5, 56 S; 427/271, 356, 358

[56] References Cited

U.S. PATENT DOCUMENTS

| | | | |
|---|---|---|---|
| 2,182,304 | 12/1939 | Rolle | 113/120 A |
| 3,110,413 | 11/1963 | McKay | 220/64 |
| 3,258,319 | 6/1966 | Cox | 72/42 |
| 3,478,554 | 11/1969 | Demsey | 72/46 |
| 3,581,539 | 6/1971 | Lavener | 72/45 |
| 3,776,848 | 12/1973 | Hall | 252/49.5 |
| 3,832,962 | 9/1974 | Rolles | 113/120 A |
| 3,833,502 | 9/1974 | Leary et al. | 252/49.5 |
| 3,873,458 | 3/1975 | Parkinson | 252/49.5 |
| 3,945,231 | 3/1976 | Imazu | 113/120 A |

FOREIGN PATENT DOCUMENTS

| | | | |
|---|---|---|---|
| 698,888 | 12/1964 | Canada | 72/42 |
| 1,270,642 | 4/1972 | United Kingdom | 72/46 |

*Primary Examiner* — Michael J. Keenan

[57] ABSTRACT

A method of forming an article from sheet metal in a press, in which method a water reducible coating is applied to the work piece in the press to serve not only as a lubricant and coolant during pressing but also as a hardenable coating on the work piece after pressing. The use of an ethyl acrylate-styrene-acrylic acid copolymer in water is described. Further coatings may be applied to the first coating either before or after hardening of the first coating.

20 Claims, 3 Drawing Figures

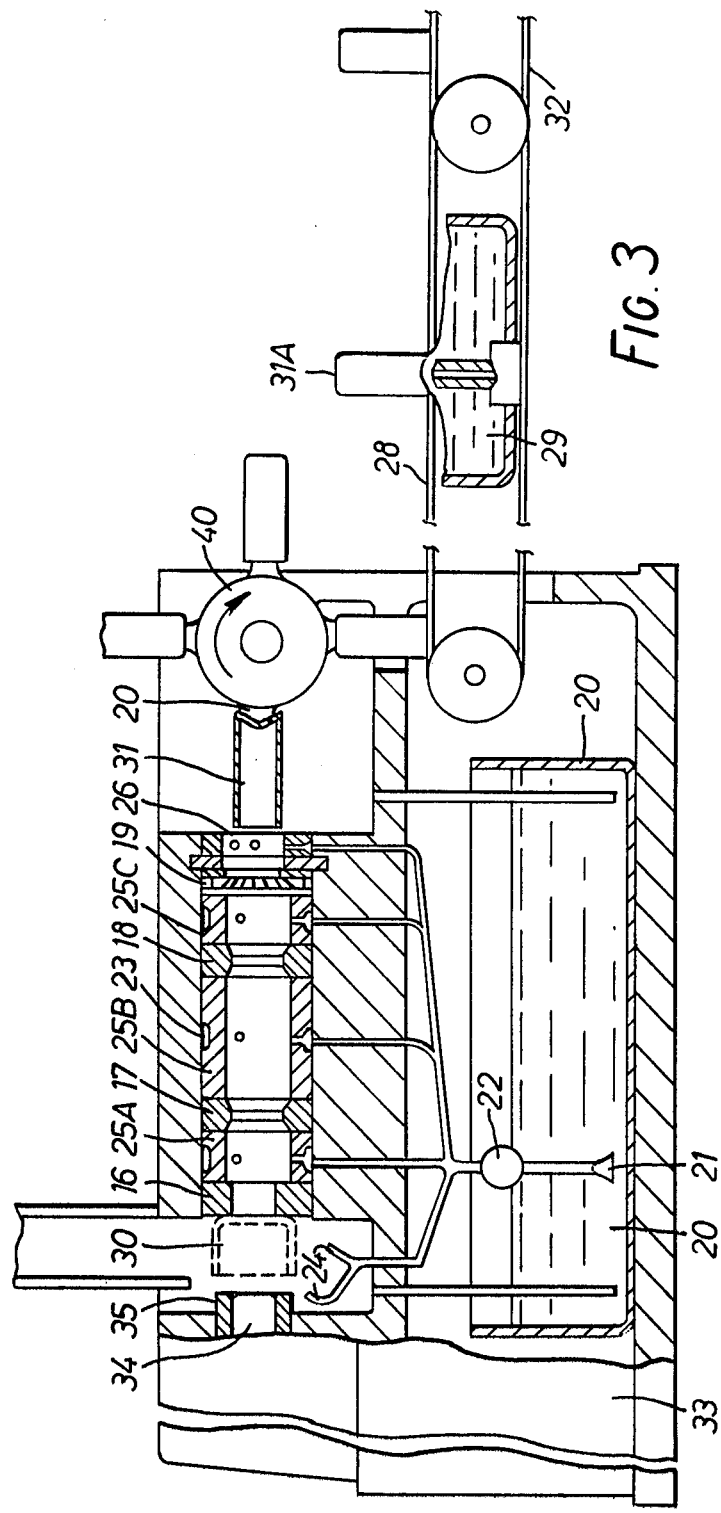

METHOD AND APPARATUS FOR FORMING A COATED CONTAINER

This invention relates to the manufacture of coated articles.

Cans are known, which are made by taking sheet metal, lubricating the sheet and blanking out a disc which is subsequently drawn to a cup by a drawing press. The cup is then placed on the punch of a wall ironing press which pushes the cup through a succession of annular dies so that the wall of the cup is progressively reduced in thickness and correspondingly increased in height to make the desired can.

Conventionally, such wall ironing presses are lubricated by means of an emulsion of oil in water, of types well known in the Industry, which is pumped from a sump and directed into the tool pack. The emulsion acts as both lubricant and coolant. After the can has been formed it is trimmed to the correct length. Then the lubricant residues are washed off and the can is dried in readiness for the application of internal and external coatings and any subsequent external decorations.

The provision of the lubricant in such a process and its subsequent removal represents a significant part of the overall cost of producing the can. Applicants have discovered that, surprisingly, the function of lubricant and coolant for at least the last of the pressing operations can be achieved by materials forming part or all of the coating of the finished can.

According to the present invention from one aspect there is provided a method of manufacturing a coated article in which sheet metal or a workpiece formed therefrom is subjected to a single pressing operation or a plurality of successive pressing operations, the said pressing operation or at least the last of the said successive pressing operations being performed using as lubricant and coolant a water reduced coating material which emerges as a hardenable coating on the pressed article.

If desired the coating may be supplemented by further coating applied after the article has been formed and either before or after the coating has hardened.

According to a further aspect the invention provides apparatus for manufacturing an article by the method defined above. The apparatus may advantageously be arranged to apply the coating material in the form of jets, and comprise heaters for hardening the coating by direct heat.

According to yet another aspect thereof the invention provides an article produced by a method or apparatus as defined above.

Various embodiments of the invention will now be described by way of example and with reference to the accompanying drawings of which:-

Figure 2:
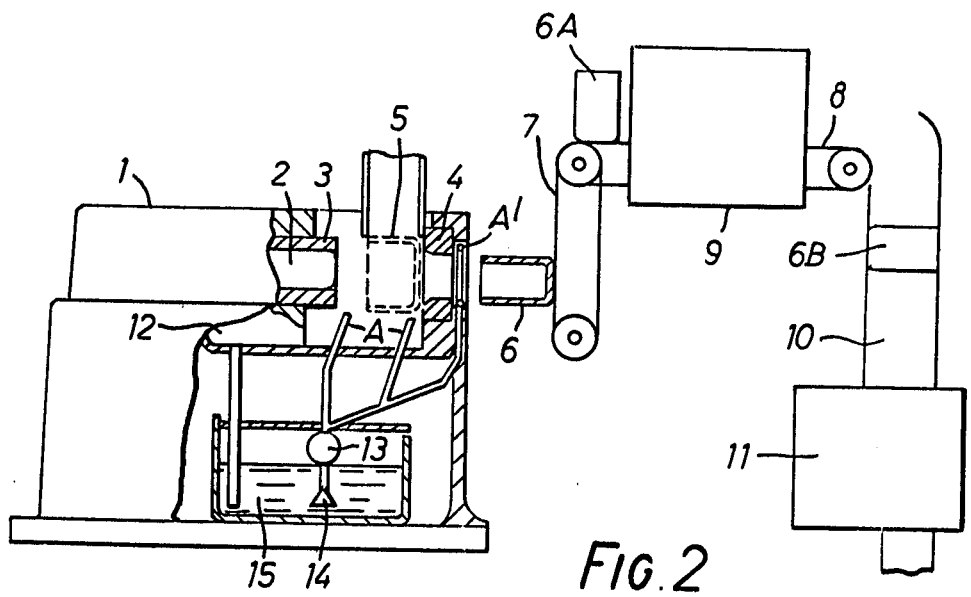

FIG. 1 is a block diagram to show two alternative methods according to the invention, FIG. 2 is a diagrammatic representation of apparatus for carrying out the first method depicted in FIG. 1; and FIG. 3 is a diagrammatic representation of apparatus for carrying out the second method depicted in FIG. 1.

Referring to FIG. 1, in one method in accordance with the invention a combined coating and lubricating material is prepared and applied to a sheet metal workpiece while in a press which forms it into an article. The article is thereafter removed from the press and stoved to harden the coating, after which the article is trimmed if desired. The lower series of blocks in FIG. 1, joined by dashed lines, indicates an alternative method wherein the article is removed from the press and washed with coating material to smooth the surface or alternatively washed with water to remove part of the coating (e.g. from the rim of the article), after which the article is dried, trimmed and passed on for any further operations.

Referring to FIG. 2, it will be seen that a press 1 for redrawing a workpiece, in the form of a cup 5, to form a can 6 has a punch 2, a blank holder 3 and a die 4. The cup 5, which has been formed from sheet metal by a previous drawing operation, is shown in line with the punch and die ready for positioning on the punch prior to drawing through the die.

Arrows A indicate sprays of a water reduced coating material which are directed into and around the cup and onto the die so as not only to form a wet coating on the cup as it emerges from the die but also to act as a lubricant and coolant for the redrawing operation. The last applicator for the coating material, represented by the arrow A', is in the form of a ring of sprays and serves to smooth the coating on the can emerging from the die 4. Alternatively this final applicator may be in the form of a circular brush which surrounds the reformed cup or can as it leaves the die 4. The coating material applied by the final applicator may also, if desired, supplement the coating material already on the can as it emerges from the die 4. The frictional forces between the cup 5 and the die 4 cause the can to leave the press 1 in a warm condition and whilst this warmth contributes to the hardening of the coating it is not generally sufficient to fully harden the coating.

Any surplus coating material is collected in a collector tray 12 from which it can drain into a sump 15. A filter 14 filters the water reducible coating before the pump 13 recirculates it to the tool pack.

Upon leaving the die 4 the can, now denoted 6, is picked up by a magnetic or vacuum conveyor 7 and carried via a second conveyor 8 through an oven 9 which is heated by a radiant elements (not shown) to harden the coating. The conveyor 7 receives the can 6 in a "wet" condition, but as the conveyor is at room temperature any drips running off the can 6 do not set to impede the conveying function. By the time the can reaches the second conveyor 8 which carries the can through the oven 9, any drips have run off the can so that the second conveyor does not become seriously fouled. The resins may be hardened by exposure to hot gases or other known means.

When the coating has been hardened to at least a handable condition, the cans (e.g. 6A) are conveyed by a conveyor 10 to a trimmer 11. The trimming operation cuts off the ears created during drawing and ensures that all the cans are of the desired height; it also removes any peripheral edge drips or runs with the trimmed shred.

In FIG. 3 apparatus is shown for carrying out the alternative method of FIG. 1 in which a workpiece, in the form of a cup 30, is simultaneously pressed and coated to make a can 31 which is thereafter partially washed before the coating is hardened by storing.

In FIG. 3 a long stroke press 33 has tools comprising a punch 34 and a blank holder 35 reciprocable towards and away from a redrawing die 16, a first ironing ring 17 a second ironing ring 18, a stripper 19 and a bottom forming block 27. The apparatus further includes a reservoir 20, which contains a water reduced coating material, and means for distributing the coating material to the tools. In FIG. 3 the means for distributing the coating material include a filter 21 a pump 22 and pipes to deliver the coating material to the tools. The filter and pump are preferably located below the level of fluid in the reservoir to minimise frothing.

The cup 30, drawn from sheet metal in a previous operation, is fed to the press 33 whereon the punch 34 and blank holder 35 enter the cup 30 and, while the blank holder holds the bottom of the cup against the face of the redrawing die 16, the punch continues its axial motion to draw the cup through the redrawing die 16 to make a cup of reduced diameter but of substantially unaltered wall thickness. The punch continues its forward axial motion to carry the redrawn cup through the first and second ironing rings 17, 18 wherein the cylindrical wall of the redrawn cup is thinned so that the sidewall of the cup becomes extended in length.

In the apparatus of FIG. 3 water reduced coating material in the reservoir is first drawn through the filter 21 by the pump 22 which then delivers coating material continuously through a nozzle 24 to the cup receiving space, in front of the redrawing die 16, where coating material is applied to the punch 34, blank holder 35 and the cup 30.

Coating material is also pumped continuously to each of the spacer blocks 25A, 25B, 25C. Each spacer block is a hollow cylinder of a length chosen to separate the die 16 and rings 17 and 18 and stripper 19 respectively. A circumferential groove, such as that denoted 23 in spacer 35B, cut in the outer cylindrical wall of each spacer block distributes the coating material around the block and radial holes allow the material to pass into the hollow space within to impinge on the cup exterior between the passage through the dies on rings 16, 17 and 18. Spacer block 25A separates the redrawing die 16 from the first ironing ring 17. Spacer 25B separates the first ironing ring from the second ironing ring 18. Spacer 25C separates the second ironing ring from the stripper 19. The coating material is delivered from the nozzle 24 and spacer blocks 25A, 25B and 25C in the form of a low velocity stream or spray, directed into the path of the punch 34.

In FIG. 3, a further coating applicator 26 is shown after the stripper 19, the purpose of which is to smooth the coating on the can emerging from the stripper. The applicator 26 may be in the form of a ring of jets or a circular brush. In a modification it is omitted.

At the end of the punch travel the bottom of the can 31 abuts against a bottom shaping block 27. After the bottom has been shaped the punch 34 retracts and the can is stripped from the punch 34 by the stripper 19 and held on the bottom shaping block 27.

The bottom shaping block 27 is one of four such blocks carried by a rotable mandrel 40. After the can has been freed from the punch 34 this mandrel is rotated in a clockwise direction as shown to carry the can away from the press and invert it before placing it on a wet conveyor 28. The conveyor 28 has a mesh belt which carries the can 31 over a washing fountain 29 which directs a wave of water of controlled height to engage with the rim of can 31A and remove any drips or runs of coating material from the rim before the can is transferred to a dry conveyor 32 for stoving. The partial washing described prevents excessive fouling of the subsequent machines such as printing machines or trimmers used to trim the rim of the can.

If desired, the press 1 of FIG. 2 may be used in conjunction with the mandrel 40, wet conveyor 28, fountain 29 and dry conveyor 32 of FIG. 3. Likewise, the press shown in FIG. 3 may be used in conjunction with the items 7 to 11 of FIG. 2.

The coated cans are then ready for any further internal spray coating or external decorations as may be thought desirable.

It will be understood that the term "water reducible coating" includes solvents, emulsions and dispersions in water. One such water reducible coating which we have used successfully for multistage wall ironing of tinplace cans is a solution of 2-10% (by volume) of a water miscible co-solvent in which is dissolved an ethyl acrylate-styrene-acrylic acid copolymer (such as that sold by Coates Bros. Ltd. as Number M1574). Similarly, we have been successful in carrying out this operation with a crosslinkable modified acrylic dispersion (such as that sold by International Pinchin Johnson Ltd. as Number 0966 C 8010R2). Optionally, reagents may be added to suppress foaming of the coating material in the press. The cans bearing these coatings were placed in an oven at 400° F for between 1 to 3 minutes to harden the coating. It is envisaged that water reducible coatings based on other resins e.g. vinyls or esters may be used instead of those based on acrylic resins, and that the coatings may be coloured by a dye if desired. The coatings applied after pressing may be pigmented.

By use of a method as particularly described a surface finish may be produced which is already receptive to printing inks and lacquers so that cleaning prior to such a process is unnecessary.

The invention has wide application to the manufacture of articles by pressing from sheet materials such as aluminum, steel and tinplate.

We claim:

1. A method of forming an externally coated container body from a starting article in a press, said method comprising the steps of placing a starting article in a press, applying a water reducible coating material to the starting article while the starting article is in the press, then actuating the press to press the starting article into the container body utilizing the coating material as both a lubricant and a coolant during the pressing with the coating material remaining on the formed container body as an overall external coating, and removing the externally coated container body from the press with the coating in a hardenable condition.

2. A method according to claim 1, wherein the coating is formed of a copolymer of ethyl acrylate-styrene-acrylic acid.

3. A method according to claim 1 wherein the coating is smoothed by washing followed by hardening of the coating.

4. A method according to claim 1 wherein a further coating is applied to the first mentioned coating followed by hardening of said first mentioned coating.

5. A method according to claim 1 wherein the coating is hardened with the hardening occurring separate from the pressing.

6. A method according to claim 1 wherein the coating is hardening with the hardening occurring separate from the pressing outside of the press.

7. A method according to claim 1 wherein said coating is smoothed subsequent to the pressing by the application of additional of the coating material.

8. A method according to claim 1 wherein the container body is heated to harden said coating after the container body is removed from said press.

9. A method according to claim 1 wherein the container body is moved in a vertical direction after removal from said press to facilitate removal of excess coating material from the container body.

10. A method accoridng to claim 1 wherein the press performs a plurality of sequential pressings, and additional coating material is applied to the container body between at least certain of the pressing.

11. A can made according to the method of claim 1.

12. A method of making a coated can from sheet metal said method comprising the steps of blanking a workpiece from the sheet metal, drawing the workpiece into a cup, redrawing the cup to a deeper cup and ironing the wall of the deeper cup to form a can, characterised in that a water reduced coating material is applied to the workpiece at least during said ironing with said water reduced coating material acting as a lubricant and coolant during said ironing, and said coating material remaining on said can as a hardenable overall external coating after said ironing.

13. A method according to claim 12 wherein the coated can is heated to harden the coating after said ironing.

14. A method according to claim 12 wherein the coating is hardened and thereafter an open end of the can is trimed and excess can material and coating are removed.

15. A method according to claim 12 wherein the can is first moved vertically after the ironing to facilitate removal of excess coating material and then the coating material is caused to be hardened.

16. A method of operating a conventional wall ironing can body maker of the type having applying means for applying a lubricant to a blank being formed therein to simultaneously form a can body and apply a primer coating to the can body, said method comprising the steps of operating the can body maker in a conventional manner to form a can body while utilizing said applying means to apply to a blank at least prior to a forming step thereon a water reduced coating material, and utilizing said coating material both as a lubricant and a coolant in addition to being a permanent overall external coating.

17. The method of claim 16 wherein the coating material remains unhardened when the can body is removed from the can body maker and the can body is thereafter heated to harden the coating.

18. The method of claim 16 wherein the coating material remains unhardened when the can body is removed from the can body maker, the can body is then washed to smooth the coating, and then the can body is heated to harden the coating.

19. An apparatus for forming a sheet metal blank into a coated can body, said apparatus comprising a can body maker including press means for drawing and forming a blank into an elongated can body, and supply means operatively associated with said can body maker for applying to a blank a combined lubricant, coolant and coating material capable of forming an overall external coating while the blank is in the can body maker and subsequent to an operation of said press means on the blank, said combined lubricant, coolant and coating material being of a type which remains adhered to the resultant can body in an unhardened state after the operation of said press means, and said apparatus including coating smoothing means for smoothing the unhardened coating to the exclusion of the sheet metal of the can body.

20. The apparatus of claim 19 wherein said smoothing means includes means for effecting a washing of a formed and coated can body.

* * * * *